United States Patent [19]
Prasad et al.

[11] Patent Number: 5,523,449
[45] Date of Patent: Jun. 4, 1996

[54] PROCESS FOR PREPARING PHOSPHORODICHLORIDO-DITHIOATES BY REACTING ALKYLMERCAPTANS WITH PHOSPHORUS TRICHLORIDE IN THE PRESENCE OF SULFUR

[75] Inventors: Vidyanatha A. Prasad; Peter E. Newallis, both of Leawood, Kans.; Emerson L. Foote, Jr., Kansas City, Mo.

[73] Assignee: Bayer Corporation, Pittsburgh, Pa.

[21] Appl. No.: 442,621

[22] Filed: May 17, 1995

[51] Int. Cl.$^6$ .................................................. C07F 9/20
[52] U.S. Cl. .................................................. 558/96
[58] Field of Search ...................................... 558/96

[56] References Cited

U.S. PATENT DOCUMENTS

| | | | |
|---|---|---|---|
| 3,879,500 | 4/1975 | Uhing et al. | 260/981 |
| 4,035,449 | 7/1977 | Zakaryan | 558/97 |
| 4,082,822 | 4/1978 | Diehr et al. | 260/972 |
| 4,120,917 | 10/1978 | Schmitt | 558/96 |
| 4,251,469 | 2/1981 | Zinke et al. | 558/96 X |
| 5,081,272 | 1/1992 | Wehrenberg | 558/90 |

FOREIGN PATENT DOCUMENTS 187785  10/1966  U.S.S.R. .

OTHER PUBLICATIONS

Houben–Weyl: "Die Methoden der Organischen Chemie" (The Methods of Organic Chemistry) vol. 12/2, p. 682 (Month unavailable) 1994, Gerorge Thieme Verlag Stuttgart.

*Primary Examiner*—Johann Richter
*Assistant Examiner*—Michael G. Ambrose
*Attorney, Agent, or Firm*—Joseph C. Gil; Godfried R. Akorli

[57] ABSTRACT

Disclosed herein is a process for preparing a phosphorodichloridodithioate comprising reacting a mercaptan with a phosphorus trichloride and sulfur in the presence of an amine catalyst.

8 Claims, No Drawings

PROCESS FOR PREPARING PHOSPHORODICHLORIDO-DITHIOATES BY REACTING ALKYLMERCAPTANS WITH PHOSPHORUS TRICHLORIDE IN THE PRESENCE OF SULFUR

BACKGROUND OF THE INVENTION

1. Field of the Invention

The present invention relates to an improved process for the preparation of phosphorodichloddodithioates that can be used as intermediates for the synthesis of insecticidally active compounds.

2. Brief Description of the Prior Art

Disclosed by the prior art is a process for preparing phosphorodichloridodithioates by heating the corresponding phosphoric acid alkyl ester dichlorides with phosphorus(V) sulfide to 140°–150° C. (see Houben-Weyl: "Die Methoden der Organischen Chemie" (The Methods of Organic Chemistry), Volume 12/2, page 682 [1964], George Thieme Verlag Stuttgart). Alternately, O-alkyl ester dichlorides can be reacted directly with phosphorus(V) sulfide to give the dithiophosphoric acid alkyl ester dichlorides.

In carrying out these processes industrially, one finds problems in separating and removing the phosphorus pentoxide by-product. After separating the resulting dithiophosphoric acid alkyl ester dichlorides, there remain solid phosphorus pentoxide and sulfur-containing, extremely malodorous compounds. Their removal to leave an odor-free product, say by oxidation in an alkaline medium, is only partially feasible, and requires long times and high costs.

Another method of preparing phosphordichloridodithioates comprises reacting elemental sulfur with thiophosphoric acid ester dichlorides that are obtained from the reaction of thiols and phosphorus trichloride. The reaction of sulfur with the thiophosphoric acid ester dichlorides only takes place at temperatures above 100° C. Sulfurization of the thiophosphoric acid ester dichlorides is attended by a marked disproportionation to dithiophosphorous acid diester chlorides and phosphorus trichloride. To suppress the disproportionation, the sulfurization must be carried out under pressure (see Houben-Weyl, loc. cit.).

U.S. Pat. No. 3,879,500 and Russian Patent No. 187,785 disclose what appears to be a simple method for preparing phosphorodichloridodithioates. The method comprises reacting corresponding thiol compounds with thiophosphoryl chloride. However, if too large an amount of the thiol compound is employed in this reaction, trithiophosphoric acid diester chlorides and tetrathiophosphoric acid esters are obtained, almost exclusively as the reaction product, even in the presence of acid-binding agents (see also Houben-Weyl, loc. cit.).

U.S. Pat. No. 4,082,822 discloses a process for the preparation of a phosphorodichloridodithioates by reacting a thiol compound with a thiophosphoryl halide in the presence of a catalyst. Distinctly, the catalyst is selected from the group consisting of a metal, an anhydrous metal halide, a Lewis acid, a nitrogen-alkylated lactam or an N,N-disubstituted carboxylic acid amide or phosphoric acid amide at a temperature of about 0° to 170° C.

DESCRIPTION OF THE INVENTION

The present invention provides an environmentally sound and high yield process for preparing phosphorodichlori-dodithioates.

The present invention now provides a highly efficient process for the preparation of phosphorodichloridodithioates of the general formula

in which
R represents a straight chain or branched alkyl radical with up to 8 carbon atoms (which is optionally substituted by alkoxy or alkylthio), a cycloaliphatic radical with 5 or 6 ring members, an aralkyl radical with 6 to 8 carbon atoms, comprising reacting:
(i) a mercaptan of the general formula R—SH in which R has the above-mentioned meaning,
(ii) a phosphorus trichloride of the formula $PCl_3$
(iii) sulfur wherein the reaction is in the presence of a tertiary amine catalyst.

The method according to the invention has a number of advantages over the known methods for the preparation of phosphorodichloridodithioates. It requires easily accessible starting materials, which can be reacted in an easily regulated one-pot process, to give high yields of the desired products. The process can be used to prepare phosphorodichloridodithioates with a variety of possible substituents. The phosphorodichloridodithioates obtainable in accordance with the process can be isolated from the reaction mixture by simple operations, such as distillation or crystallization. Advantageously, the process does not pollute the environment. The by-product hydrogen chloride can be removed easily and the catalysts can be recycled repeatedly. Hence, it is not necessary to discharge the catalysts from the reaction vessel after they have been used once.

The mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan. More preferably, the mercaptan is propyl mercaptan.

In carrying out the process, the reactants are employed in an effective ratio to produce the phosphorodichloridodithioates. The phosphorus trichloride can be employed in a mole ratio of 1.0 to 1.5 and preferably 1.0 to 1.1 mole per mole of the mercaptan. Sulfur can be employed in a mole ratio of 1.0 mole per mole of phosphorus trichloride.

The catalysts that are useful herein are base catalysts which are typically amines. The amines can be selected from the group consisting of pyridines such as 5-ethyl-2-methylpyridine, 2-methylpyridine, 2,4-dimethylpyridine, 2,6-dimethylpyridine or 2,4,6-trimethylpyridine; trialkylamines such as tri-n-propylamine and tri-n-butylamine. Preferred herein as the catalyst are 5-ethyl-2-methylpyridine and tri-n-butylamine. Amounts of 0.005 to 0.05 mole of the catalyst per mole of the mercaptan can be employed.

The use of a solvent or diluent when carrying out the process is not necessary, but halogenated hydrocarbons, such as monochlorobenzene or dichlorobenzene, can be employed.

In the following illustrative but non-limiting embodiment of the invention, the process comprises reacting n-propylmercaptan, phosphorus trichloride and sulfur as starting materials. The reaction can be conducted at initial temperatures of about 50° C. to 80° C. and preferably 55° C. to 60° C. wherein the following reaction occurs.

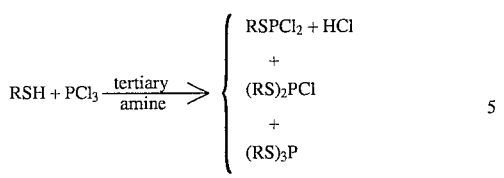

At higher temperatures, all the reagents including PCl$_3$ react with sulfur and this reaction results in the conversion of trivalent phosphorus compounds to pentavalent phosphorus compounds. The higher temperatures are in the range of 60° C. to 150° C. and preferably 90° C. to 140° C. The reaction at the higher temperatures can be as follows:

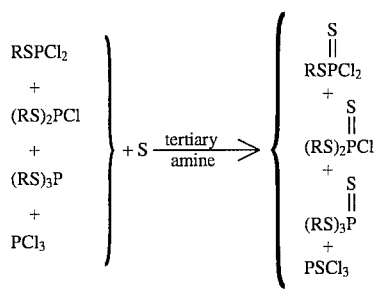

The following equilibration reactions, which also generate the phosphorodichloridodithioate, occur at elevated temperatures as well.

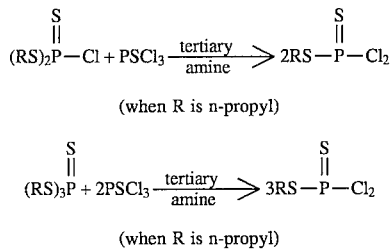

After completion of the reaction and after distilling excess thiophosphoryl halide and the phosphorodichloridodithioates, the distillation heel which contains the catalyst, is again reacted with phosphorus trichloride, sulfur and the mercaptan without adding a substantial amount of fresh catalyst. The process for the preparation of the phosphorodichloridodithioates (which are to be purified by distillation) can therefore be carried out by recycling the heel containing catalyst. In general, phosphorodichloridodithioates are liquid and can be separated by distillation under reduced pressure.

As can be seen from the foregoing, the process of the invention can be characterized by the advantages of: using starting materials, phosphorous trichloride, sulfur and mercaptan which are readily available articles of commerce; and using a tertiary amine catalyst which produces a fluid heel on distillation of the reaction mixture. In accordance with the invention, the phosphorodichloridodithioates can be prepared in high yield under environmentally desirable and cost-effective (moderate) reaction conditions. In the practice of the invention, the phosphorodichloridodithioates may be used as intermediates for the synthesis of insecticidal thiophosphoric acid esters.

The invention is further illustrated but is not intended to be limited by the following examples in which all parts and percentages are by weight unless otherwise specified.

EXAMPLES

Example 1

Synthesis of n-Propylphosphorodichloridodithioate via the reaction of n-Propylmercaptan with PCl$_3$ and S Catalyzed by 5-ethyl-2-methylpyridine

| Charges: | | | |
|---|---|---|---|
| | PCl$_3$ | 137.0 g | (1.0 mol) |
| | Sulfur | 32.06 | (1.0 mol) |
| | 5-ethyl-2-methylpyridine | 1 g | |
| | n-Propylmercaptan | 76.16 g | (1.0 mol) |

Procedure

To a 1,000 ml 4-necked round bottomed flask, fitted with an overhead stirrer, thermometer, addition funnel, brine cooled condenser (−5° C.), NaOH scrubber system and a nitrogen inlet line, was charged 137.0 g (1.0 mol) of PCl$_3$ and 32.06 g of sulfur. The resulting mixture was well agitated. This is followed by the addition of 1.0 g of 5-ethyl-2-methylpyridine catalyst to the mixture. The temperature of the mixture was raised gradually to 55°–60° C. To this reaction mixture was added 76.16 g (1.0 mol) of n-Propylmercaptan over a period of 1 hour using a gentle nitrogen flow. The final ratio of moles of PCl$_3$ to moles of n-Propyl-mercaptan was 1.52; the additional PCl$_3$ being supplied by the "heels" recycled from the previous batch. (Heels can be prepared by reaching PCl$_3$, S, and mercaptan at 90° to 110° C. in the presence of the catalyst.) The reaction temperature was gradually raised to 145° C. and the mixture cooked at this temperature for 4 hours.

The reaction mixture was subjected to vacuum distillation (10 mmHg). A forecut (mostly PSCl$_3$) was collected over a temperature range of 25°–79° C. A main cut was collected over a temperature range of 95°–110° C. and it analyzed as 90% ester dichloride. A heel residue comprising

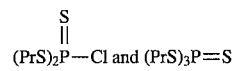

as the main constituents was saved for the next batch. The crude product was further refined via vacuum distillation at 10 mmHg. PSCl$_3$ and dipropyldisulfide (DPDS) were collected as forecuts, the ester dichloride was collected as the main-cut while the higher boiling components were retained in the "heel". The forecuts and the "heel" residues were all combined for recycle to the subsequent batch.

The distilled product analyzed 96.5% active ingredient (by gas/liquid chromatography) and contained 0.5% PSCl$_3$, 0.3% dipropyldisulfide, and 0.7%.

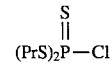

This process was repeated over 30 batches using no additional 5-ethyl-2-methylpyridine in subsequent batches. The yield of distilled product, over 30 batches, amounted to 96.0% based on propylmercaptan charged.

Examples 2–5

In the following examples, there were employed essentially the same procedure and evaluation as described in Example 1. The results are listed in the following tables.

| Catalyst* | Run No. | % RS—$\overset{\overset{S}{\|}}{P}Cl_2$ | % DPDS | % Yield on n-PrSH | Comments |
|---|---|---|---|---|---|
| MEP | 1 | 46.2 | 0.2 | 84.2 | A.I. 97.3 |
|  | 2 | 56.1 | 0.3 | 93.2 | (distilled Product) |
|  | 3 | 61.7 | 0.3 | 96.2 |  |
|  | 4 | 61.8 | 0.3 | 97.1 |  |
| 2,4-Lutidine | 1 | 46.7 | 0.3 | 82.1 | A.I. 97.1% |
|  | 2 | 56.2 | 0.4 | 92.5 | (distilled Product) |
|  | 3 | 61.5 | 0.3 | 96.1 |  |
|  | 4 | 61.8 | 0.3 | 96.8 |  |

| Catalyst* | Run No. | % RS—$\overset{\overset{S}{\|}}{P}Cl_2$ | % DPDS | % Yield on PrSH | Comments |
|---|---|---|---|---|---|
| 2,6-Lutidine | 1 | 45.2 | 0.3 | 81.8 | A.I. 97.1% |
|  | 2 | 56.4 | 0.3 | 92.6 | (distilled Product)** |
|  | 3 | 61.3 | 0.3 | 96.1 |  |
|  | 4 | 61.7 | 0.2 | 96.6 |  |
| Tributylamine | 1 | 47.1 | 0.3 | 83.7 | A.I. 97.3% |
|  | 2 | 56.5 | 0.3 | 93.1 | (distilled Product)** |
|  | 3 | 61.8 | 0.3 | 96.5 |  |
|  | 4 | 61.8 | 0.3 | 97.5 |  |
| N,N-dimethyl-benzylamine | 1 | 46.1 | 0.3 | 82.4 | A.I. 97.1% |
|  | 2 | 55.8 | 0.3 | 92.1 | (distilled Product)** |
|  | 3 | 61.4 | 0.3 | 95.9 |  |
|  | 4 | 61.6 | 0.3 | 96.4 |  |

*1 g of a tertiary amine was used as a catalyst per mole of n-PrSH.
**Distillation residue (heel) was fluid at room temperature over several recycles.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of phosphorodichlorididodithioates of the general formula

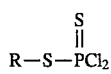

in which

R represents a straight chain or branched alkyl radical with up to 8 carbon atoms which is optionally substituted by alkoxy or alkylthio, a cycloaliphatic radical with 5 or 6 ring members, or an aralkyl radical with 6 to 8 carbon atoms, comprising reacting:

(i) a mercaptan of the general formula R—SH in which R has the above-mentioned meaning, (ii) phosphorus trichloride, and (iii) sulfur, wherein the reaction is conducted in the presence of a tertiary amine catalyst.

2. The process of claim 1 wherein the amine is selected from the group consisting of 5-ethyl-2-methylpyridine, 2-methylpyridine, 2,4-dimethylpyridine, 2,6-dimethylpyridine, 2,4,6-trimethylpyridine, tri-n-propylamine, tri-n-butylamine.

3. The process of claim 2 wherein the amine is 5-ethyl-2-methylpyridine.

4. The process of claim 2 wherein the amine is tri-n-butylamine.

5. The process of claim 1 wherein the mercaptan is an alkyl mercaptan selected from the group consisting of methyl mercaptan, ethyl mercaptan, n-propyl mercaptan, isopropyl mercaptan, n-butyl mercaptan, sec-butyl mercaptan, t-butyl mercaptan and isobutyl mercaptan.

6. The process of claim 5 wherein the mercaptan is n-propyl mercaptan.

7. The process of claim 1 further comprising distilling the phosphorodichloridithioate and a by-product thiophosphoryl chloride to provide a fluid distillation heel containing catalyst.

8. The process of claim 7 comprising reacting the distillation heel with a mercaptan and thiophosphoryl chloride and phosphorus trichloride without a substantial addition of a fresh catalyst.

* * * * *